US011433046B2

(12) United States Patent
Tu et al.

(10) Patent No.: US 11,433,046 B2
(45) Date of Patent: Sep. 6, 2022

(54) COMPOSITIONS AND METHODS FOR TREATING EPILEPSY, SEIZURES AND OTHER CONDITIONS

(71) Applicant: TULEX PHARMACEUTICALS INC., Cranbury, NJ (US)

(72) Inventors: Yu-Hsing Tu, West Windsor, NJ (US); Ashok Perumal, Monmouth Junction, NJ (US); Kalyan Kathala, Monroe, NJ (US); Romona Bhattacharya, Franklin Park, NJ (US)

(73) Assignee: Tulex Pharmaceuticals Inc., Cranbury, NJ (US)

( * ) Notice: Subject to any disclaimer, the term of this patent is extended or adjusted under 35 U.S.C. 154(b) by 0 days.

(21) Appl. No.: 17/308,910

(22) Filed: May 5, 2021

(65) Prior Publication Data

US 2021/0251952 A1    Aug. 19, 2021

Related U.S. Application Data

(62) Division of application No. 16/999,772, filed on Aug. 21, 2020, now abandoned.

(60) Provisional application No. 62/946,260, filed on Dec. 10, 2019.

(51) Int. Cl.
| | | |
|---|---|---|
| *A61K 31/357* | (2006.01) | |
| *A61K 9/08* | (2006.01) | |
| *A61K 47/10* | (2017.01) | |
| *A61K 47/34* | (2017.01) | |
| *A61J 1/06* | (2006.01) | |
| *A61J 7/00* | (2006.01) | |
| *A61K 9/00* | (2006.01) | |

(52) U.S. Cl.
CPC ............. *A61K 31/357* (2013.01); *A61J 1/06* (2013.01); *A61J 7/0023* (2013.01); *A61J 7/0046* (2013.01); *A61J 7/0053* (2013.01); *A61K 9/0053* (2013.01); *A61K 9/08* (2013.01); *A61K 47/10* (2013.01); *A61K 47/34* (2013.01)

(58) Field of Classification Search
CPC combination set(s) only.
See application file for complete search history.

(56) References Cited

U.S. PATENT DOCUMENTS

| | | | |
|---|---|---|---|
| 6,559,293 B1 | 5/2003 | Almarsson et al. | |
| 9,205,194 B2 | 12/2015 | Mojdehbakhsh et al. | |
| 2003/0077227 A1* | 4/2003 | Dugger, III | A61P 25/00 424/43 |
| 2005/0129765 A1 | 6/2005 | Li et al. | |
| 2006/0270611 A1* | 11/2006 | Dries | A61K 31/35 514/23 |
| 2015/0343153 A1 | 12/2015 | Granelli | |
| 2017/0043019 A1 | 2/2017 | Cloyd | |
| 2018/0093040 A1 | 4/2018 | Thorne et al. | |
| 2020/0315962 A1 | 10/2020 | Endo et al. | |
| 2020/0383911 A1 | 12/2020 | Sudhakar et al. | |
| 2021/0069107 A1 | 3/2021 | Sudhakar et al. | |

FOREIGN PATENT DOCUMENTS

| | | | |
|---|---|---|---|
| CN | 106109408 | 11/2016 | |
| WO | WO 2002/102369 | 12/2002 | |
| WO | WO 2005/048981 | 6/2005 | |
| WO | WO-2005048981 A1 * | 6/2005 | A61P 25/00 |
| WO | WO 2006/125774 | 11/2006 | |
| WO | WO-2019186515 A1 | 10/2019 | |
| WO | WO-2020053662 A2 | 3/2020 | |
| WO | WO-2020104837 A1 | 5/2020 | |

OTHER PUBLICATIONS

Doose et al., "Single-dose pharmacokinetics and effect of food on the bioavailability of topiramate, a novel antiepileptic drug," J Clin Pharmacol. Oct. 1996;36(10):884-91.*
Pinto et al., "Topiramate: A Review of Analytical Approaches for the Drug Substance, Its Impurities and Pharmaceutical Formulations," Journal of Chromatographic Science., vol. 54, No. 2, pp. 280-290, (2015).
Rosemont Pharmaceuticals Ltd. (2019). *DCPAR Topiramate Rosemont 10 & 20mg/ml Oral Suspension* [Public Assessment Report].
The United States Pharmacopeial Convention. (2017). *Packaging and Storage Requirements* [Bulletin].
Trokendi XR [package insert]. Rockville, MD: Supernus Pharmaceuticals, Inc.; 2019.

* cited by examiner

*Primary Examiner* — Jared Barsky
(74) *Attorney, Agent, or Firm* — Wilson Sonsini Goodrich & Rosati

(57) ABSTRACT

Compositions are provided for the liquid oral administration of topiramate and its salts. The invention further provides methods for treating diseases and disorders using the compositions.

17 Claims, 1 Drawing Sheet

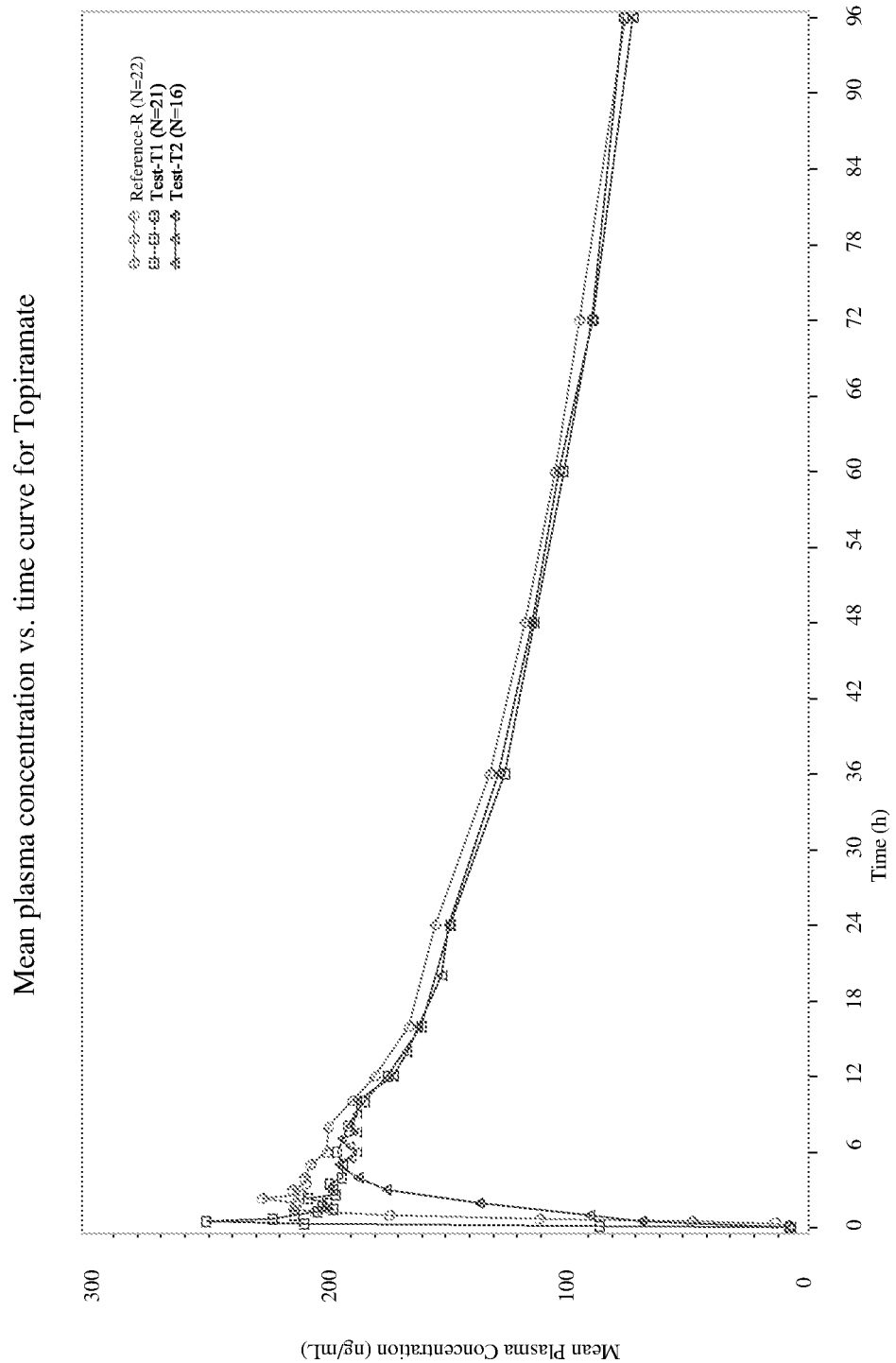

COMPOSITIONS AND METHODS FOR TREATING EPILEPSY, SEIZURES AND OTHER CONDITIONS

CROSS REFERENCE TO RELATED APPLICATIONS

This application is a divisional of U.S. application Ser. No. 16/999,772, filed Aug. 21, 2020, which claims benefit of U.S. Provisional Application No. 62/946,260, filed on Dec. 10, 2019, the content of each of which is incorporated herein by reference in its entirety.

FIELD

The disclosure herein relates to pharmaceutical compositions comprising topiramate, or a pharmaceutically acceptable addition salt thereof, delivery devices comprising the pharmaceutical compositions, and to methods for treating conditions and disorders including epilepsy, tremors, seizures including partial-onset seizures, primary or secondary generalized seizures, primary generalized tonic-clonic seizures, seizures associated with Lennox-Gastaut syndrome, treatment and prevention of migrant headaches, treatment of mood disorders such as depression, manias, bipolar disorder, borderline personality disorder, obesity, eating disorders such as binge eating, antipsychotic-induced weight gain, post-traumatic stress disorder, Type II diabetes, tobacco cessation, alcohol dependence and neuropathic pain using the compositions and devices.

BACKGROUND

Topiramate is 2,3:4,5-Di-O-isopropylidine-β-D-fructopyranose sulfamate, and has the following chemical structure:

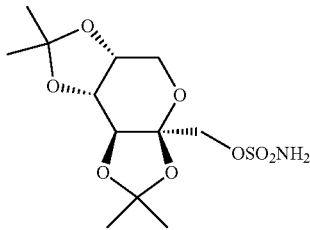

Topiramate has been approved in the United States as therapy for the treatment of epilepsy, tremors, and seizures including partial-onset seizures, primary generalized tonic-clonic seizures, seizures associated with Lennox-Gastaut syndrome.

Topiramate is also known to be useful in treatment and prevention of migraine headaches, and is frequently prescribed for that purpose. Topiramate is also known to be useful for treatment of mood disorders such as depression, manias and bipolar disorder, and in the treatment of borderline personality disorder, obesity, eating disorders such as binge eating, antipsychotic-induced weight gain, post-traumatic stress disorder, Type II diabetes, and tobacco cessation, and neuropathic pain.

Topiramate is a white crystalline powder that is known to be soluble in alkaline solutions containing sodium hydroxide or sodium phosphate, acetone, dimethylsulfoxide and ethanol. In water, topiramate has a solubility of about 9.8 mg/ml. However, topiramate is not stable in aqueous solution, and therefore has been heretofore formulated primarily in solid dosage forms such as capsules and tablets from which water can easily be excluded. One example of topiramate is the formulation currently sold under the tradename Topamax™ by Ortho-McNeil Pharmaceutical, Inc., Raritan, N.J. Topiramate, which is a tablet solid dosage form available in amounts of 25, 50, 100, 200, 300, and 400 mg.

International Patent Application WO/2006/125774 describes a liquid pediatric formulation of topiramate that is prepared as a "preconcentrate" which contains a relatively low water content, and which is diluted with water to provide dosages for administration to a pediatric patient.

There exists an ongoing need for more efficacious delivery of topiramate, and in particular, for a ready-to-use room temperature and atmospheric oxygen stable adult or pediatric oral liquid formulation. This invention is directed to these, as well as other, important ends.

SUMMARY

It has been discovered in accordance with the present invention that a liquid formulation containing a therapeutically effective amount of topiramate, or a pharmaceutically acceptable addition salt thereof, can be prepared that can be administered orally, is stable at room temperature for at least two years, and can be administered to a patient without the need for further dilution.

Thus, in one embodiment, the present disclosure provides a liquid pharmaceutical composition (Composition 1) comprising:
topiramate, or a pharmaceutically acceptable addition salt thereof, in an amount of from about 1.2% w/v (i.e., 12 mg/ml) to about 10% w/v (i.e., 100 mg/ml), for example from about 2.5% w/v (i.e., 25 mg/ml) to about 10% w/v (i.e., 100 mg/ml); and
a solvent component comprising one or more organic solvents in an amount of from about 80% to about 120% w/v;
wherein the pharmaceutical composition is substantially anhydrous. In some further embodiments (Composition 1a), the total amount of water present in the composition is 0.35% w/w or less.

The present disclosure further provides the following pharmaceutical compositions:

1.1 Composition 1 or 1a, wherein the pharmaceutical composition is a liquid for oral administration;
1.2 Composition 1 or 1a, wherein the total amount of water present in the composition is from about 0.001% to about 0.35% w/w; or from about 0.01% to about 0.3% w/w; or from about 0.1% to about 0.3% w/w, or from about 0.15% to about 0.25% w/w; or from about 0.2% to about 0.25% w/w, or about 0.22% w/w;
1.3 Any of Compositions 1, 1a and 1.1-1.2, wherein the composition is stable for at least 24 months at 20-25° C.;
1.4 Any of Compositions 1, 1a and 1.1-1.2, wherein the composition is stable for at least 24 months at controlled room temperature;
1.5 Any of Compositions 1, 1a and 1.1-1.4, wherein the topiramate is in the form of a free acid;
1.6 Any of Compositions 1, 1a and 1.1-1.5, wherein the topiramate, or a pharmaceutically acceptable addition salt thereof, is present in an amount of from about 1.2% to about 3.0% w/v, for example from about from 1.2% to about 2.5% w/v, for example about 2.0% to about 3.0% w/v;

1.7 Any of Compositions 1, 1a and 1.1-1.6, wherein the topiramate, or a pharmaceutically acceptable addition salt thereof, is present in an amount of about 1.2 to about 2.5% w/v;

1.8 Any of Compositions 1, 1a and 1.1-1.6, wherein the topiramate, or a pharmaceutically acceptable addition salt thereof, is present in an amount of about 2.5% w/v;

1.9 Any of Compositions 1, 1a and 1.1-1.8, wherein the organic solvents are selected from polyethers, lower polyhydroxy alcohols, ethanol, propylene glycol, isosorbide dimethyl ether, di(ethylene glycol) ethyl ether, mineral oil; light mineral oil; glycols, such as glycerol behenate and polyethylene glycols (PEGs), hydrogenated vegetable oil, including cottonseed oil, sunflower oil, sesame oil, olive oil, corn oil, soybean oil, and mixtures thereof;

1.10 Composition 1.9, wherein the organic solvents are selected from glycerin, polyethylene glycols of molecular weight 300 to 8000, propylene glycol, and mixtures thereof;

1.11 Composition 1.9, wherein the organic solvents are selected from glycerin, polyethylene glycols of molecular weight from about 300 to about 3000; or from 300 to about 1000; or from about 300 to about 600, or from 300 to about 500, or about 400;

1.12 Composition 1.9, wherein the organic solvents are selected from glycerin and polyethylene glycols of molecular weight about 400;

1.13 Composition 1.12, wherein the glycerin is present in the composition in an amount of about 60% to about 70%, or about 60% to about 65%, or about 63%, and the polyethylene glycol of molecular weight about 400 is present in the composition in an amount of about 40% to about 60%, or about 45% to about 55%, or about 50%;

1.14 Any of Compositions 1 and 1.1-1.13, further comprising one or more preservatives selected from parabens, benzyl alcohol, benzoic acid, sorbic acid, sodium benzoate, sodium sorbate and antibacterial agents selected from halogenated diphenyl ether (e.g. triclosan), herbal extracts and essential oils (e.g., rosemary extract, tea extract, *magnolia* extract, thymol, menthol, eucalyptol, geraniol, carvacrol, citral, hinokitol, catechol, methyl salicylate, epigallocatechin gallate, epigallocatechin, gallic acid, miswak extract, seabuckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, phthalic acid, monoperthalic acid and its esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, and mixtures of any of the foregoing;

1.15 Composition 1.14, wherein the preservatives comprise one or more of methylparaben, propylparaben, benzoic acid, a benzoate salt, sorbic acid and ascorbic acid salt.

1.16 Any of Compositions 1, 1a and 1.1-1.15, further comprising a sweetener component, the sweetener component comprising one or more sweeteners;

1.17 Composition 1.16, wherein the sweetener component is present in an amount of from about 0.5% to about 2% w/v;

1.18 Composition 1.16 or 1.17, wherein the sweeteners are selected from sucralose aspartame, polyols such as mannitol, sorbitol and xylitol, acesulfame, neotame, *stevia*, dextrose, saccharin sodium, fructose, high fructose corn syrup, maltodextrin and sucrose;

1.19 Any of Compositions 1, 1a and 1.1-1.18 further comprising a flavor component, the flavor component comprising one or more flavor compounds;

1.20 Composition 1.19, wherein the flavor component is present in an amount of from about 0.1% to about 0.5% w/v.

1.21 Any of the foregoing Compositions, comprising the following components:
polyethylene glycol 400 in an amount of about 50% w/v;
a paraben component comprising one or more parabens, the paraben component being in an amount of about 2.4% w/v;
glycerin in an amount of about 40% w/v to about 70% w/v;
topiramate, or a pharmaceutically acceptable addition salt thereof, in an amount of about 1.2% to about 2.5% w/v, for example about 2.5% w/v;
one or more sweeteners in an amount of about 1% w/v; and
a flavor component comprising one or more flavor compounds, the flavor component being in an amount of about 0.2% w/v;

1.22 Composition 1.21, consisting essentially of the following components:
polyethylene glycol 400 in an amount of about 50% w/v;
a paraben component comprising one or more parabens, the paraben component being in an amount of about 2.4% w/v;
glycerin in an amount of about 40% w/v to about 70% w/v;
topiramate, or a pharmaceutically acceptable addition salt thereof, in an amount of about 1.2% to about 2.5% w/v, for example about 2.5% w/v;
one or more sweeteners in an amount of about 1% w/v; and
a flavor component comprising one or more flavor compounds, the flavor component being in an amount of about 0.2% w/v.

1.23 Composition 1.21, wherein the glycerin is present in an amount of about 60% w/v to about 65% w/v; for example about 63% w/v;

1.24 Composition 1.22, wherein the glycerin is present in an amount of about 60% w/v to about 65% w/v; for example about 63% w/v;

1.25 Any of Compositions 1.14-1.24, wherein the parabens comprise methylparaben and propylparaben, and the sweetener comprises sucralose.

1.26 Any of Compositions 1, 1a and 1.1-1.25, wherein the composition has one or more of the following features:
a refractive index of from about 1.3 to about 1.38;
a viscosity of 300-600 cps, for example 450 cps; or
a density of 1.1-1.3, for example about 1.2 g/ml;

1.27 Any of the foregoing Compositions, comprising the following components:
polyethylene glycol 400 in an amount of about 50% w/v;

a preservative component in an amount of about 2.4% w/v;
glycerin in an amount of about 63% w/v;
topiramate in an amount of about 2.5% w/v;
a sweetener component in an amount of about 2.4% w/v;
a preservative component in an amount of about 1% w/v; and
a flavor component in an amount of about 0.2% w/v;

1.28 Any of the foregoing Compositions, consisting essentially of the following components:
polyethylene glycol 400 in an amount of about 50% w/v;
a preservative component in an amount of about 2.4% w/v;
glycerin in an amount of about 63% w/v;
topiramate in an amount of about 2.5% w/v;
a sweetener component in an amount of about 2.4% w/v;
a preservative component in an amount of about 1% w/v; and
a flavor component in an amount of about 0.2% w/v;

1.29 Any of the foregoing Compositions, consisting of the following components:
polyethylene glycol 400 in an amount of about 50% w/v;
a preservative component in an amount of about 2.4% w/v;
glycerin in an amount of about 63% w/v;
topiramate in an amount of about 2.5% w/v;
a sweetener component in an amount of about 2.4% w/v;
a preservative component in an amount of about 1% w/v; and
a flavor component in an amount of about 0.2% w/v;

1.30 Any of Compositions 1, 1a and 1.1-1.29, wherein the composition contains no added water;

1.31 Any of Compositions 1, 1a and 1.1-1.29, wherein the pH of the composition has not been adjusted;

1.32 Any of Compositions 1, 1a and 1.1-1.29, wherein the composition is ready to use.

1.33 Any of Compositions 1, 1a and 1.1-1.32, wherein a composition having topiramate in an amount of 2.5% w/v (i.e., 25 mg/ml) is bioequivalent to TOPAMAX® 25 mg commercially available capsule.

1.34 Any of Compositions 1, 1a and 1.1-1.33, wherein the topiramate, or pharmaceutically acceptable addition salt thereof, is present in an amount of about 2.5% w/v (i.e., 25 mg/ml); and the composition exhibits a total amount of topiramate absorbed that is bioequivalent to a commercially available capsule (TOPAMAX®) composition containing 25 mg of topiramate upon administration to a human subject, wherein the bioequivalence of the total amount of topiramate absorbed is established by a 90% confidence interval for $AUC_{0-\infty}$ and $AUC_{0-t}$ which is between 80% and 125% upon administration with or without food.

1.35 Any of Compositions 1, 1a and 1.1-1.34 wherein the composition is bioequivalent to commercially available TOPAMAX® capsule.

1.36 Any of Compositions 1, 1a and 1.1-1.35, wherein: when the topiramate, or pharmaceutically acceptable addition salt thereof, is present in an amount of about 2.5% w/v (i.e., 25 mg/ml), the composition exhibits: a fasting median T max (in hours) of from about 0.3 to about 1.25, or from about 0.3 to about 1.0, or from about 0.3 to about 0.7, or about 0.5; and/or a fed median T max (in hours) of from about 3 to about 8, or from about 4 to about 7, or from about 5 to about 6, or about 5.5.

1.37 Any of Compositions 1, 1a and 1.1-1.36, wherein the composition exhibits a fasting median T max (in hours) of from about 0.3 to about 0.7, or about 0.5; and/or a fed median T max (in hours) of from about 5 to about 6, or about 5.5.

1.38 Any of Compositions 1, 1a and 1.1-1.37, wherein the composition exhibits a fasting median T max (in hours) of from about 0.3 to about 0.7, or about 0.5; and a fed median T max (in hours) of from about 5 to about 6, or about 5.5.

The present disclosure further provides a liquid pharmaceutical composition (Composition 2) for use in the treatment of a disease or disorder, or symptom thereof, selected from epilepsy, tremors, seizures including partial-onset seizures, primary or secondary generalized seizures, primary generalized tonic-clonic seizures, seizures associated with Lennox-Gastaut syndrome, treatment and prevention of migraine headaches, treatment of mood disorders such as depression, manias, bipolar disorder, borderline personality disorder, obesity, eating disorders such as binge eating, antipsychotic-induced weight gain, post-traumatic stress disorder, Type II diabetes, tobacco cessation, alcohol dependence and neuropathic pain, the composition comprising:
topiramate, or a pharmaceutically acceptable addition salt thereof, in an amount of from about 1.2% w/v (i.e., 12 mg/ml) to about 10% w/v (i.e., 100 mg/ml), for example from about 2.5% w/v (i.e., 25 mg/ml) to about 10% w/v (i.e., 100 mg/ml); and
a solvent component comprising one or more organic solvents in an amount of from about 80% to about 120% w/v;
wherein the pharmaceutical composition is substantially anhydrous. In some further embodiments (Composition 2a), the total amount of water present in the composition is 0.35% or less.

The present disclosure further provides the following pharmaceutical compositions:

2.1 Composition 2 or 2a, wherein the pharmaceutical composition is a liquid for oral administration;

2.2 Composition 2 or 2a, wherein the total amount of water present in the composition is from about 0.001% to about 0.35% w/w; or from about 0.01% to about 0.3% w/w; or from about 0.1% to about 0.3% w/w, or from about 0.15% to about 0.25% w/w; or from about 0.2% to about 0.25% w/w, or about 0.22% w/w;

2.3 Any of Compositions 2 or 2a and 2.1-2.2, wherein the composition is stable for at least 24 months at 20-25° C.;

2.4 Any of Compositions 2 or 2a and 2.1-2.2, wherein the composition is stable for at least 24 months at controlled room temperature;

2.5 Any of Compositions 2 or 2a and 2.1-2.4, wherein the topiramate is in the form of a free acid;

2.6 Any of Compositions 2 or 2a and 2.1-2.5, wherein the topiramate, or a pharmaceutically acceptable addition salt thereof, is present in an amount of from about 1.2% to about 3.0% w/v, for example from about 2.0% to about 3.0% w/v;

2.7 Any of Compositions 2 or 2a and 2.1-2.6, wherein the topiramate, or a pharmaceutically acceptable addition salt thereof, is present in an amount of about 1.2 to about 2.5% w/v;

2.8 Any of Compositions 2 or 2a and 2.1-2.6, wherein the topiramate, or a pharmaceutically acceptable addition salt thereof, is present in an amount of about 2.5% w/v 2.9 Any of Compositions 2 or 2a and 2.1-2.8, wherein the organic solvents are selected from polyethers, lower polyhydroxy alcohols, ethanol, propylene glycol, isosorbide dimethyl ether, di(ethylene glycol) ethyl ether, mineral oil; light mineral oil; glycols, such as glycerol behenate and polyethylene glycols (PEGs), hydrogenated vegetable oil, including cottonseed oil, sunflower oil, sesame oil, olive oil, corn oil, soybean oil, and mixtures thereof;

2.10 Composition 2.9, wherein the organic solvents are selected from glycerin, polyethylene glycols of molecular weight 300 to 8000, propylene glycol, and mixtures thereof;

2.11 Composition 2.9, wherein the organic solvents are selected from glycerin, polyethylene glycols of molecular weight from about 300 to about 3000; or from 300 to about 1000; or from about 300 to about 600, or from 300 to about 500, or about 400;

2.12 Composition 2.9, wherein the organic solvents are selected from glycerin and polyethylene glycols of molecular weight about 400;

2.13 Composition 2.12, wherein the glycerin is present in the composition in an amount of about 60% to about 70%, or about 60% to about 65%, or about 63%, and the polyethylene glycol of molecular weight about 400 is present in the composition in an amount of about 40% to about 60%, or about 45% to about 55%, or about 50%, 2.14 Any of Compositions 2 or 2a and 2.1-2.13, further comprising one or more preservatives selected from parabens, benzyl alcohol, benzoic acid, sorbic acid, sodium benzoate, and antibacterial agents selected from halogenated diphenyl ether (e.g. triclosan), herbal extracts and essential oils (e.g., rosemary extract, tea extract, *magnolia* extract, thymol, menthol, eucalyptol, geraniol, carvacrol, citral, hinokitol, catechol, methyl salicylate, epigallocatechin gallate, epigallocatechin, gallic acid, miswak extract, sea-buckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, phthalic acid, monoperthalic acid and its esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, and mixtures of any of the foregoing;

2.15 Composition 2.14, wherein the preservatives comprise methylparaben and propylparaben.

2.16 Any of Compositions 2 or 2a and 2.1-2.15, further comprising a sweetener component, the sweetener component comprising one or more sweeteners;

2.17 Composition 2.16, wherein the sweetener component is present in an amount of from about 0.5 to about 2% w/v;

2.18 Composition 2.16 or 2.17, wherein the sweeteners are selected from sucralose aspartame, polyols such as mannitol, sorbitol and xylitol, acesulfame, neotame, *stevia*, dextrose, saccharin sodium, fructose, high fructose corn syrup, maltodextrin and sucrose;

2.19 Any of Compositions 2 or 2a and 2.1-2.18, further comprising a flavor component, the flavor component comprising one or more flavor compounds.

2.20 Composition 2.19, wherein the flavor component is present in an amount of from about 0.1 to about 0.5% w/v.

2.21 Any of the foregoing Compositions, comprising the following components:
polyethylene glycol 400 in an amount of about 50% w/v;
a paraben component comprising one or more parabens, the paraben component being in an amount of about 1.2% to about 2.5% w/v, for example about 2.4% w/v;
glycerin in an amount of about 40% w/v to about 70% w/v;
topiramate, or a pharmaceutically acceptable addition salt thereof, in an amount of about 2.5% w/v;
one or more sweeteners in an amount of about 1% w/v; and
a flavor component comprising one or more flavor compounds, the flavor component being in an amount of about 0.2% w/v.

2.22 Composition 2.21, consisting essentially of the following components:
polyethylene glycol 400 in an amount of about 50% w/v;
a paraben component comprising one or more parabens, the paraben component being in an amount of about 2.4% w/v;
glycerin in an amount of about 40% w/v to about 70% w/v;
topiramate, or a pharmaceutically acceptable addition salt thereof, in an amount of about 1.2%-2.5% w/v, for example about 2.5% w/v;
one or more sweeteners in an amount of about 1% w/v; and
a flavor component comprising one or more flavor compounds, the flavor component being in an amount of about 0.2% w/v.

2.23 Composition 2.21, wherein the glycerin is present in an amount of about 60% w/v to about 65% w/v; for example about 63% w/v;

2.24 Composition 2.22, wherein the glycerin is present in an amount of about 60% w/v to about 65% w/v; for example about 63% w/v;

2.25 Any of Compositions 2.14 or 2.24, wherein the parabens comprise methylparaben and propylparaben, and the sweetener comprises sucralose.

2.26 Any of Compositions 2 or 2a and 2.1-2.25, wherein the composition has one or more of the following features:
a refractive index of from about 1.3 to about 1.38
a viscosity of 300-600 cps, for example 450 cps; or
a density of 1.1-1.3, for example about 1.2 g/ml.

2.27 Any of the foregoing Compositions, comprising the following components:
polyethylene glycol 400 in an amount of about 50% w/v;
a preservative component in an amount of about 2.4% w/v;
glycerin in an amount of about 63% w/v;
topiramate in an amount of about 2.5% w/v;
a sweetener component in an amount of about 2.4% w/v;
a preservative component in an amount of about 1% w/v; and a flavor component in an amount of about 0.2% w/v;
2.28 Any of the foregoing Compositions, consisting essentially of the following components:
polyethylene glycol 400 in an amount of about 50% w/v;
a preservative component in an amount of about 2.4% w/v;
glycerin in an amount of about 63% w/v;
topiramate in an amount of about 2.5% w/v;
a sweetener component in an amount of about 2.4% w/v;
a preservative component in an amount of about 1% w/v; and
a flavor component in an amount of about 0.2% w/v;
2.29 Any of the foregoing Compositions, consisting of the following components:
polyethylene glycol 400 in an amount of about 50% w/v;
a preservative component in an amount of about 2.4% w/v;
glycerin in an amount of about 63% w/v;
topiramate in an amount of about 2.5% w/v;
a sweetener component in an amount of about 2.4% w/v;
a preservative component in an amount of about 1% w/v; and
a flavor component in an amount of about 0.2% w/v;
2.30 Any of Compositions 2 or 2a and 2.1-2.29, wherein the composition contains no added water;
2.31 Any of Compositions 2 or 2a and 2.1-2.30, wherein the pH of the composition has not been adjusted.
2.32 Any of Compositions 2 or 2a and 2.1-2.31, wherein the composition is ready to use.
2.33 Any of Compositions 2, 2a and 2.1-2.32, wherein a composition having topiramate in an amount of 2.5% w/v (i.e., 25 mg/ml) is bioequivalent to TOPAMAX® 25 mg commercially available capsule.
2.34 Any of Compositions 2, 2a and 2.1-2.33, wherein the topiramate, or pharmaceutically acceptable addition salt thereof, is present in an amount of about 2.5% w/v (i.e., 25 mg/ml); and the composition exhibits a total amount of topiramate absorbed that is bioequivalent to a commercially available capsule (TOPAMAX®) composition containing 25 mg of topiramate upon administration to a human subject, wherein the bioequivalence of the total amount of topiramate absorbed is established by a 90% confidence interval for $AUC_{0-\infty}$ and $AUC_{0-t}$ which is between 80% and 125% upon administration with or without food.
2.35 Any of Compositions 2, 2a and 2.1-2.34, wherein the composition is bioequivalent to commercially available TOPAMAX® capsule.
2.36 Any of Compositions 2, 2a and 2.1-2.35, wherein: when the topiramate, or pharmaceutically acceptable addition salt thereof, is present in an amount of about 2.5% w/v (i.e., 25 mg/ml), the composition exhibits: a fasting median T max (in hours) of from about 0.3 to about 1.25, or from about 0.3 to about 1.0, or from about 0.3 to about 0.7, or about 0.5; and/or a fed median T max (in hours) of from about 3 to about 8, or from about 4 to about 7, or from about 5 to about 6, or about 5.5.
2.37 Any of Compositions 2, 2a and 2.1-2.36, wherein the composition exhibits a fasting median T max (in hours) of from about 0.3 to about 0.7, or about 0.5; and/or a fed median T max (in hours) of from about 5 to about 6, or about 5.5.
2.38 Any of Compositions 2, 2a and 2.1-2.37, wherein the composition exhibits a fasting median T max (in hours) of from about 0.3 to about 0.7, or about 0.5; and a fed median T max (in hours) of from about 5 to about 6, or about 5.5.

In one embodiment, Compositions 1, 1a, 1.1-1.38, 2, 2a and 2.1-2.38 are provided as ready-to-use liquid preparations. As used herein, the term "ready-to-use" is intended to mean that the composition is administered to the patient without dilution, and/or without the addition of any further components to the composition.

In some embodiments described herein, the composition may only include additional ingredients that do not materially affect the basic and novel characteristics of the composition. For example, the oral care composition may consist essentially of a compositions 1, 1a, 1.1-1.38, 2, 2a or 2.1-2.38, and additional ingredients that do not materially affect one or more of the efficacy of the composition, or the bioequivalence of the composition to commercially available TOPAMAX® capsule.

In some embodiments, a desired amount of Composition 1, 1a, 1.1-1.38, 2, 2a or 2.1-2.38 can be stored in a dosage dispensing unit. As used herein, the term "dosage dispensing unit" is intended to mean a container that is known in the medical arts to be useful for storing liquid pharmaceuticals prior to administration, and from which portions of the contents, for example specific doses to be administered to a patient, can be withdrawn. Examples of such dosage dispensing units include, but are not limited to, bottles, ampoules, vials, syringes, etc.

Thus, the present disclosure also provides a dosage dispensing unit (Dosage dispensing unit 1), that contains a composition according to any of compositions 1, 1a, 1.1-1.38, 2, 2a and 2.1-2.38 described above.

The present disclosure further provides the following dosage dispensing units:
1.1 Dosage dispensing unit 1, wherein the dosage dispensing unit is a bottle, an ampoule, a vial, or a syringe;
1.2 Dosage dispensing unit 1, wherein the dosage dispensing unit is a bottle comprising:
a removable cap, for example a screw cap or snap-on cap; or
a septum; or
a metered dispensing cap;
1.3 Dosage dispensing unit 1 or 1.1-1.2, wherein the dosage dispensing unit is a bottle with a septum adapted to allow removal of liquid;
1.4 Dosage dispensing unit 1.3, wherein the septum allows removal of liquid by use of a syringe;
1.5 Dosage dispensing unit 1.4, wherein the syringe is an oral syringe.

In some embodiments, a desired amount of Composition 1, 1a, 1.1-1.38, 2, 2a or 2.1-2.38 is withdrawn from a dosage dispensing unit, and administered to a patient. In some embodiments, the Composition 1, 1a, 1.1-1.38, 2, 2a or 2.1-2.38 is withdrawn from the dosage dispensing unit by use of a direct dosing device. As used herein, the term "direct dosing device" is intended to mean a device or container that is used to administer its contents directly to a patient. Examples of such direct dosing devices include, but are not limited to, syringes, for example oral syringes, cups for example dosing cups, an ampoule, a vial, a syringe, spoons for example dosage spoons, teaspoons and tablespoons, a dropper or dropper assembly, a pipette, a measuring device with graduations, or any device customarily used for, or capable of being used to dispense a liquid medicament to a patient. Such devices, including dosage cups, dosage spoons, droppers and dropper assemblies, oral syringes, bottles with fitments, and total dispensing systems are sold by Comar, Voorhees, N.J. Examples of the foregoing dosage cups, dosage spoons, droppers and dropper assemblies, oral syringes, and total dispensing systems can be found on the Comar website at www.comar.com., the O. Berk website at www.oberk.com, and the Drug Plastic website at www.drugplastics.com.

Thus, the present disclosure also provides a direct dosing device (Direct dosing device 1), that contains a composition according to any of compositions 1, 1a, 1.1-1.38, 2, 2a or 2.1-2.38 described above.

The present disclosure further provides the following direct dosing devices:

1.1 Direct dosing device 1, wherein the direct dosing device is a syringe;
1.2 Direct dosing device 1 or 1.1, wherein the direct dosing device is an oral syringe;
1.3 Any of direct dosing devices 1 or 1.1-1.2, wherein the direct dosing device contains a desired amount of Composition 1, 1a, 1.1-1.38, 2, 2a or 2.1-2.38 for direct administration to a patient;
1.4 Direct dosing device 1, wherein the direct dosing device is a cup;
1.5 Direct dosing device 1, wherein the direct dosing device is a dosing cup;
1.6 Direct dosing device 1, wherein the direct dosing device is an ampoule;
1.7 Direct dosing device 1, wherein the direct dosing device is a vial;
1.8 Direct dosing device 1, wherein the direct dosing device is a spoon;
1.9 Direct dosing device 1, wherein the direct dosing device is a dosage spoon, teaspoon or tablespoon;
1.10 Direct dosing device 1, wherein the direct dosing device is a spoon having graduations to indicate contained volume;
1.11 Direct dosing device 1, wherein the direct dosing device is a dropper;
1.12 Direct dosing device 1, wherein the direct dosing device is a pipette;
1.13 Direct dosing device 1, wherein the direct dosing device is a measuring device with graduations;
1.14 Direct dosing device 1, wherein the direct dosing device is a device customarily used for dispensing a liquid medicament to a patient;
1.15 Any of direct dosing devices 1 or 1.1-1.14, wherein the direct dosing device contains from 12 mg to 1000 mg of topiramate or a pharmaceutically acceptable addition salt thereof, or from 12 mg to 25 mg of topiramate or a pharmaceutically acceptable addition salt thereof, or from 25 mg to 1000 mg of topiramate or a pharmaceutically acceptable addition salt thereof, or from 25 mg to 800 mg of topiramate or a pharmaceutically acceptable addition salt thereof, or from 25 mg to 600 mg of topiramate or a pharmaceutically acceptable addition salt thereof, or from 25 mg to 400 mg or topiramate or a pharmaceutically acceptable addition salt thereof, or from 25 mg to 200 mg or topiramate or a pharmaceutically acceptable addition salt thereof;
1.16 Any of direct dosing devices 1 or 1.1-1.15, wherein the direct dosing device contains from 12 mg to 25 mg of topiramate, or a pharmaceutically acceptable addition salt thereof;
1.17 Any of direct dosing devices 1 or 1.1-1.15, wherein the direct dosing device contains from 25 mg to 400 mg of topiramate, or a pharmaceutically acceptable addition salt thereof;
1.18 Any of direct dosing devices 1 or 1.1-1.15, wherein the direct dosing device contains from 12 mg to 200 mg of topiramate, for example from 25 mg to 200 mg of topiramate, or a pharmaceutically acceptable addition salt thereof;
1.19 Any of direct dosing device 1 or 1.1-1.15, wherein the direct dosing device contains 12, mg, 14 mg, 16 mg, 18 mg, 20 mg, 22 mg, 25 mg, 50 mg, 75 mg, 100 mg, 150 mg, 200 mg, 300 mg or 400 mg of topiramate, or a pharmaceutically acceptable addition salt thereof;

In some embodiments, the direct dosing device is a syringe, for example an oral syringe, containing a desired amount of Composition 1, 1a, 1.1-1.38, 2, 2a or 2.1-2.38. The syringe can be pre-loaded with a desired amount of Composition 1, 1a, 1.1-1.38, 2, 2a or 2.1-2.38, for example a dose of the topiramate composition to be administered to the patient, or can be filled with a desired amount of Composition 1, 1a, 1.1-1.38, 2, 2a or 2.1-2.38, for example a dose of the topiramate composition to be administered to the patient, at the point of administration by, for example, withdrawal from a dosage dispensing unit according to dosage dispensing unit 1 or 1.1-1.5 described above.

The present disclosure further provides methods for using the Compositions described herein. In some embodiments, the present disclosure provides a Method (Method 1) for treating a disease or disorder, or a symptom thereof, comprising orally administering to a patient in need thereof a liquid pharmaceutical composition according to any of Compositions 1, 1a, 1.1-1.38, 2, 2a or 2.1-2.38, wherein the disease or disorder, or symptom thereof, is selected from: epilepsy, tremors, seizures including partial-onset seizures, primary or secondary generalized seizures, primary generalized tonic-clonic seizures, seizures associated with Lennox-Gastaut syndrome, treatment and prevention of migrant headaches, treatment of mood disorders such as depression, manias, bipolar disorder, borderline personality disorder, obesity, eating disorders such as binge eating, antipsychotic-induced weight gain, post-traumatic stress disorder, Type II diabetes, tobacco cessation, alcohol dependence and neuropathic pain.

The present disclosure further provides the following Methods:

1.1 Method 1, wherein the liquid pharmaceutical composition according to any of Compositions 1, 1a, 1.1-1.38, 2, 2a or 2.1-2.38 is administered to the patient from a direct dosing device;
1.2 Method 1.1, wherein the direct dosing device is selected from any of direct dosing devices 1 or 1.1-1.19;
1.3 Method 1.1, wherein the direct dosing device is an oral syringe, a cup for example a dosing cup, a vial, a spoon for example a dosage spoon, a teaspoon or tablespoon, or a dropper.
1.4 Any of Methods 1 or 1.1-1.3, wherein the liquid pharmaceutical composition according to any of Compositions 1, 1a, 1.1-1.38, 2, 2a or 2.1-2.38 is administered to the patient without dilution.
1.5 Any of Methods 1 or 1.1-1.4, wherein the patient is not a pediatric patient (i.e., is not younger than 17);
1.6 Any of Methods 1 or 1.1-1.4, wherein the patient is a pediatric patient;
1.7 Any of Methods 1 or 1.1-1.4, wherein the patient is from 2-9 years old;

1.8 Any of Methods 1 or 1.1-1.4, wherein the patient is at least 10 years old;

1.9 Any of Methods 1 or 1.1-1.4, wherein the patient is from 2-16 years old;

1.10 Any of Methods 1 or 1.1-1.4, wherein the patient is an adult;

1.11 Any of Methods 1 or 1.1-1.10, further comprising the step of filling the direct dosing device with the composition of any of Compositions 1, 1a, 1.1-1.38, 2, 2a or 2.1-2.38 by withdrawing said Composition from a dosage dispensing unit according to Dosage dispensing unit 1 or 1.1-1.5 as described herein;

1.12 Any of Methods 1 or 1.1-1.11, wherein the amount of the pharmaceutical composition administered to the patient is sufficient to provide from 12 mg to 1000 mg of topiramate or a pharmaceutically acceptable addition salt thereof, or from 12 mg to 25 mg of topiramate, or a pharmaceutically acceptable addition salt thereof, or from 25 mg to 1000 mg of topiramate or a pharmaceutically acceptable addition salt thereof, or from 25 mg to 800 mg of topiramate or a pharmaceutically acceptable addition salt thereof, or from 25 mg to 600 mg of topiramate or a pharmaceutically acceptable addition salt thereof, or from 25 mg to 400 mg or topiramate or a pharmaceutically acceptable addition salt thereof, or from 25 mg to 200 mg or topiramate or a pharmaceutically acceptable addition salt thereof, or 12, mg, 14 mg, 16 mg, 18 mg, 20 mg, 22 mg, 25 mg, 50 mg, 75 mg, 100 mg, 150 mg or 200 mg of topiramate, or a pharmaceutically acceptable addition salt thereof, to the patient.

The present disclosure further provides a Method (Method 2) for administering topiramate, or a pharmaceutically acceptable addition salt thereof, to a patient in need thereof, the method comprising orally ingesting a liquid pharmaceutical composition according to any of Compositions 1, 1a, 1.1-1.38, 2, 2a or 2.1-2.38.

The present disclosure further provides the following Methods:

2.1 Method 2, wherein the liquid pharmaceutical composition according to any of Compositions 1, 1a, 1.1-1.38, 2, 2a or 2.1-2.38 is administered to the patient from a direct dosing device;

2.2 Method 2.1, wherein the direct dosing device is selected from any of direct dosing devices 1 or 1.1-1.18;

2.3 Method 2.1, wherein the direct dosing device is an oral syringe, a cup for example a dosing cup, a vial, a spoon for example a dosage spoon, teaspoon, tablespoon, or a dropper.

2.4 Any of Methods 2 or 2.1-2.3, wherein the liquid pharmaceutical composition according to any of Compositions 1, 1a, 1.1-1.38, 2, 2a or 2.1-2.38 is administered to the patient without dilution.

2.5 Any of Methods 2 or 2.2-2.4, wherein the patient is not a pediatric patient;

2.6 Any of Methods 2 or 2.2-2.4, wherein the patient is a pediatric patient;

2.7 Any of Methods 2 or 2.2-2.4, wherein the patient is from 2-9 years old;

2.8 Any of Methods 2 or 2.2-2.4, wherein the patient is at least 10 years old;

2.9 Any of Methods 2 or 2.2-2.4, wherein the patient is at from 2-16 years old;

2.10 Any of Methods 2 or 2.2-2.4, wherein the patient is an adult;

2.11 Any of Methods 2.1-2.10, further comprising the step of filling the direct dosing device with a desired amount of the composition of any of Compositions 1, 1, 1a, 1.1-1.38, 2, 2a or 2.1-2.38, by withdrawing said Composition from a dosage dispensing unit according to Dosage dispensing unit 1 or 1.1-1.5 described above;

2.12 Method 2.11, wherein the direct dosing device is an oral syringe; and the dosage dispensing unit is a bottle with a septum;

2.13 Any of Methods 2 or 2.1-2.12, wherein the amount of the pharmaceutical composition administered to the patient is sufficient to provide from 12 mg to 1000 mg of topiramate or a pharmaceutically acceptable addition salt thereof, or from 12 mg to 25 mg of topiramate, or a pharmaceutically acceptable addition salt thereof, or from 25 mg to 1000 mg of topiramate or a pharmaceutically acceptable addition salt thereof, or from 25 mg to 800 mg of topiramate or a pharmaceutically acceptable addition salt thereof, or from 25 mg to 600 mg of topiramate or a pharmaceutically acceptable addition salt thereof, or from 25 mg to 400 mg or topiramate or a pharmaceutically acceptable addition salt thereof, or from 25 mg to 200 mg or topiramate or a pharmaceutically acceptable addition salt thereof, or 12, mg, 14 mg, 16 mg, 18 mg, 20 mg, 22 mg, 25 mg, 50 mg, 75 mg, 100 mg, 150 mg or 200 mg of topiramate, or a pharmaceutically acceptable addition salt thereof, to the patient.

The present disclosure further provides a Method (Method 3) for preparing a liquid pharmaceutical composition comprising topiramate, the method comprising:

a) combining at least the following components:
topiramate, or a pharmaceutically acceptable addition salt thereof, in an amount of from about 1.2% w/v (i.e., 12 mg/ml) to about 10% w/v (i.e., 100 mg/ml), for example from about 2.5% w/v (i.e., 25 mg/ml) to about 10% w/v (i.e., 100 mg/ml;

a solvent component comprising one or more organic solvents in an amount of from about 80% to about 120% w/v; and one or more preservatives; and, optionally, one or more sweeteners and/or flavors to form the liquid pharmaceutic composition;

wherein the pharmaceutical composition is substantially anhydrous.

The present disclosure further provides the following Methods:

3.1 Method 3, wherein the liquid pharmaceutic composition is a composition of any of Compositions 1, 1a, 1.1-1.38, 2, 2a or 2.1-2.38;

3.2 Method 3 or 3.1, further comprising the step of c) transferring a portion of the topiramate formulation to a direct dosing device without dilution.

3.3 Method 3.2, wherein the direct dosing device is selected from any of direct dosing devices 1 or 1.1-1.18;

3.4 Method 3.2, wherein the direct dosing device is an oral syringe, a cup for example a dosing cup, a vial, a spoon for example a dosage spoon, teaspoon, tablespoon, or a dropper.

3.5 Any of Methods 3 or 3.1-3.4, further comprising the step of administering the liquid pharmaceutical composition to a patient from the direct dosing device without dilution;

3.6 Method 3.5, wherein the patient is not a pediatric patient;

3.7 Methods 3.5, wherein the patient is a pediatric patient;

3.8 Method 3.5, wherein the patient is from 2-9 years old;
3.9 Method 3.5, wherein the patient is at least 10 years old;
3.10 Method 3.5, wherein the patient is at from 2-16 years old;
3.11 Method 3.5, wherein the patient is an adult;
3.12 Any of Methods 3 or 3.1-3.10, wherein the portion of the topiramate formulation is transferred to the direct dosing device is the dosage administered to the patient, without dilution;
3.13 Method 3.12, wherein the direct dosing device is an oral syringe, and the dosage dispensing unit is a bottle with a septum;
3.14 Any of methods 3 and 3.1-3.13, wherein the risk of contamination is reduced relative to a regime where the topiramate formulation requires dilution prior to administration.

The present disclosure further provides a Method (Method 4) for reducing risk of microbial contamination of a pharmaceutical composition comprising topiramate, or a pharmaceutically acceptable addition salt thereof, the method comprising:
  a) combining:
    topiramate, or a pharmaceutically acceptable addition salt thereof, in an amount of from about 1.2% w/v (i.e., 12 mg/ml) to about 10% w/v (i.e., 100 mg/ml), for example from about 2.5% w/v (i.e., 25 mg/ml) to about 10% w/v (i.e., 100 mg/ml); and
    a solvent component comprising one or more organic solvents in an amount of from about 80% to about 120% w/v, to form a topiramate formulation;
  b) sealing the topiramate formulation in a dosage dispensing unit; and
  c) transferring a portion of the topiramate formulation to a direct dosing device without dilution;
    wherein the pharmaceutical composition is substantially anhydrous;
    wherein the pharmaceutical composition is a liquid for oral administration; and
    wherein the risk of contamination is reduced relative to a regime where the topiramate formulation requires dilution prior to administration.

The present disclosure further provides the following Methods:
4.1 Method 4, wherein the liquid pharmaceutical composition is a composition according to any of Compositions 1, 1a, 1.1-1.38, 2, 2a or 2.1-2.38;
4.2 Method 4 or 4.1, wherein the direct dosing device is selected from any of direct dosing devices 1 or 1.1-1.18;
4.3 Method 4.1, wherein the direct dosing device is an oral syringe, a cup for example a dosing cup, a vial, a spoon for example a dosage spoon, teaspoon, tablespoon, or a dropper;
4.4 Any of Methods 4 or 4.1-4.3, further comprising the step of administering the composition to the patient from the direct dosing device without dilution.
4.5 Method 4.4, wherein the patient is not a pediatric patient;
4.6 Methods 4.4, wherein the patient is a pediatric patient;
4.7 Method 4.4, wherein the patient is from 2-9 years old;
4.8 Method 4.4, wherein the patient is at least 10 years old;
4.9 Method 4.4, wherein the patient is at from 2-16 years old;
4.10 Method 4.4, wherein the patient is an adult; 4.11 Any of Methods 4 or 4.1-4.7, wherein the direct dosing device is an oral syringe; and the dosage dispensing unit is a bottle with a septum.

The present disclosure also provides the use of a composition as described herein in the preparation of a medicament for the treatment of any of the disease or disorders, or symptom thereof, as disclosed herein.

BRIEF DESCRIPTION OF THE DRAWINGS

FIG. 1 depicts the mean plasma concentration vs. time curve for Topiramate Oral Solution 25 mg/mL in accordance with the present disclosure versus commercially available TOPAMAX® (Topiramate capsule).

DETAILED DESCRIPTION

Unless defined otherwise, all technical and scientific terms used herein have the same meaning as is commonly understood by one of ordinary skill in the art to which this invention belongs. In the event that there is a plurality of definitions for a term herein, those in this section prevail unless stated otherwise.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease). In some embodiments, "preventing" or "prevention" refers to reducing symptoms of the disease, disorder or condition by administering a composition as described herein. The therapeutic application for preventing or prevention of a disease of disorder is known as 'prophylaxis.'

"Patient" refers to a human being. In some embodiments, the patient is not a pediatric human. In some embodiments, the patient is an adult human. As used herein, the term "adult human" is intended to mean a human of age 17 or older. The term "pediatric" when used to describe a human patient, indicates that the human patient is from 2-16 years old.

"Treating" or "treatment" of any disease or disorder refers, in some embodiments, to ameliorating the disease or disorder (i.e., arresting or reducing the development of the disease or at least one of the clinical symptoms thereof). Treatment may also be considered to include preemptive or prophylactic administration to ameliorate, arrest or prevent the development of the disease or at least one of the clinical symptoms. In a further feature the treatment rendered has lower potential for long-term side effects over multiple years. In other embodiments "treating" or "treatment" refers to ameliorating at least one physical parameter, which may not be discernible by the patient. In yet other embodiments, "treating" or "treatment" refers to inhibiting the disease or disorder, either physically, (e.g., stabilization of a discernible symptom), physiologically, (e.g., stabilization of a physical parameter) or both. In yet other embodiments, "treating" or "treatment" refers to delaying the onset of the disease or disorder.

The term "administering" and "applying to the patient" as used in connection with the methods of the invention is intended to mean introducing a topiramate containing composition as described herein to the oral cavity of a patient, for example, by the patient, a physician, a physical therapist or other appropriate health care provider.

"Therapeutically effective amount" means the amount of topiramate, or a pharmaceutically acceptable addition salt thereof, that when administered to or administered by a patient for treating a disease or condition as described herein, is sufficient to effect such treatment for the disease.

The "therapeutically effective amount" will vary depending on the age, weight, adsorption, distribution, metabolism and excretion etc., of the patient to be treated.

Unless otherwise indicated, molecular weights given for components of the compositions described herein are expressed as grams per mole.

Pharmaceutically acceptable base addition salts of topiramate include Group I and Group II metal salts such as sodium, potassium, lithium, calcium, aluminum and magnesium salts. Preparation of topiramate, and additional topiramate base addition salts, are disclosed in U.S. Pat. No. 6,559,293, and the references cited therein. See also PCT International Application Publication Nos. WO2003/070738 and WO2003/006467, each of which is incorporated herein by reference in their entireties.

In some preferred embodiments, topiramate is present in the compositions described herein in its free acid form. Where dosage amounts of topiramate salts are given by weight, e.g., milligrams per day or milligrams per unit dose, the dosage amount of the salt is given as the weight of the corresponding free acid, unless otherwise indicated. For example, a dose of 200 mg of a topiramate base addition salt would indicate the amount of such salt that provides 200 mg of the topiramate free acid.

Pharmaceutical compositions of the present disclosure are extremely stable. In some embodiments, the present topiramate compositions are stable for at least 24 months at 20-25° C., or for at least 24 months at controlled room temperature. As used herein, the term "controlled room temperature" is intended to have the definition provided in U.S. Pharmacopeia (USP) 659 "Packaging and Storage Requirements" Rev. Bull. May 1, 2017—i.e., wherein the temperature maintained thermostatically that encompasses at the usual and customary working environment of 20°-25° C. (68°-77° F.), with the following conditions also applying: the mean kinetic temperature does not exceed 25° C. (77° F.); excursions between 15° and 30° C. (59° and 86° F.) that are experienced in pharmacies, hospitals, and warehouses, and during shipping are allowed, provided the mean kinetic temperature does not exceed 25° C., and wherein transient spikes up to 40° C. are permitted as long as they do not exceed 24 hours.

The Environmental Assessment and Finding of No Significant Impact for Topamax® (topiramate) Tablet for the Topamax® NDA, available at https://www accessdata.fda.gov/drugsatfda_docs/nda/96/020505_000_environmental_rvw.pdf and incorporated herein by reference in it is entirety, describes a series of studies of, inter alia, the degradation of topiramate in aqueous solution. The results from these studies indicate that topiramate degrades in aqueous solution by hydrolysis. The degradation proceeds first by hydrolysis of the sulfamate to give diacetone fructose along with sulfamic and sulfuric acids. Hydrolysis of the acetonides of diacetone fructose gives rise to two possible mono-acetonides and to fructose. The hydrolysis half-life of topiramate is calculated to be approximately 80 days at pH 8 and 35° C. The fructose can then undergo acid catalyzed degradation.

In addition, topiramate is known to be sensitive to oxidation. For example, International Patent Application WO/2006/125774 describes a topiramate preconcentrate which is diluted prior to use. The preconcentrate is said to include antioxidants or complex forming agents, and also deaeration and/or sparging with inert gas to reduce potential reaction with atmospheric oxygen. See WO/2006/125774 at pages 6-7.

In contrast, it has been discovered in accordance with the present disclosure that a stable, ready to use Topiramate solution can be prepared as described herein. Specifically, it has been discovered in accordance with the present disclosure that the exclusion of any added water, and/or the removal of water, from the composition confers Topiramate stability even in the presence of atmospheric oxygen. The present invention thus provides a ready-to-use oral liquid solution which is stable at room temperature, and which is stable even in the presence of atmospheric oxygen at room temperature for up to two years. While not wishing to be bound by a particular theory, it is believed that the exclusion of any added water from the compositions of the present disclosure greatly reduce the amount of both hydrolysis, and oxidation due to atmospheric oxygen.

Accordingly, the compositions of the present disclosure are "substantially anhydrous." As applied to a composition described herein, "substantially anhydrous" is intended to mean that the composition does not contain any added water, other than the traces of water that might exist in the various components of the formulation as a consequence of their processes of manufacture. The present substantially anhydrous compositions contain less than about 0.5% w/w total water, including any trace water present in the various components of the formulation. In some embodiments, the total amount of water present in the composition is about 0.35% w/w or less; from about 0.001% to about 0.35% w/w; or from about 0.01% to about 0.3% w/w; or from about 0.1% to about 0.3% w/w, or from about 0.15% to about 0.25% w/w; or from about 0.2% to about 0.25% w/w, or about 0.22% w/w; or the composition is devoid of detectable water.

Because the compositions of the present disclosure do not contain water, the pH of the present compositions are not adjusted; i.e., the composition does not contain any added aqueous acid or base. This is in contrast to some prior formulations of topiramate, for example the pediatric preconcentrate topiramate composition disclosed in International Patent Application WO/2006/125774, in which the pH of the preconcentrate is adjusted to a specific value by addition of aqueous acid or base.

The compositions of the present disclosure can include a preservative component, that can include one or more preservatives. The preservatives can be selected from any preservative known to be suitable in the pharmaceutical arts for use in liquid formulations. Suitable preservatives include parabens, which are a well-known series of antimicrobial p-hydroxybenzoate preservatives, including methyl p-hydroxybenzoate (methylparaben), ethyl p-hydroxybenzoate (ethylparaben), propyl p-hydroxybenzoate (propylparaben) and butyl p-hydroxybenzoate (butylparaben). In some embodiments, the preservative component is a mixture of methylparaben and propylparaben. Other suitable preservatives include antibacterial agents selected from halogenated diphenyl ether (e.g. triclosan), herbal extracts and essential oils (e.g., rosemary extract, tea extract, *magnolia* extract, thymol, menthol, eucalyptol, geraniol, carvacrol, citral, hinokitol, catechol, methyl salicylate, epigallocatechin gallate, epigallocatechin, gallic acid, miswak extract, sea-buckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, phthalic acid, monoperthalic acid and its esters, ascorbyl stearate, oleoyl sarcosine, alkyl sulfate, dioctyl sulfosuccinate, salicylanilide, domiphen bromide, delmopinol, octapinol and other piperidino derivatives, niacin preparations, and mixtures of any of the foregoing. The preservatives can be present in the present topiramate compositions in amounts of from about 0.01% to about 3% w/v, most typically from about 0.01% to about 0.2% w/v. In some embodiments, the preservative component is present in an amount of from 2% to 3% w/v, for example about 2.4% w/v.

The compositions of the present disclosure can include antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

The compositions of the present disclosure can include a flavor component, that can include one or more flavorants, or flavors. As used herein, the terms "flavor" or "flavorant" is intended to mean a compound used to impart a pleasant flavor and often odor to a pharmaceutical preparation. Exemplary flavoring agents or flavorants include synthetic flavor oils and flavoring aromatics and/or natural oils, extracts from plants, leaves, flowers, fruits and so forth and combinations thereof. These may also include cinnamon oil, oil of wintergreen, peppermint oils, clove oil, bay oil, anise oil, *eucalyptus*, thyme oil, cedar leave oil, oil of nutmeg, oil of sage, oil of bitter almonds and *cassia* oil. Other useful flavors include vanilla, citrus oil, including lemon, orange, grape, lime and grapefruit, and fruit essences, including apple, pear, peach, strawberry, raspberry, cherry, plum, pineapple, apricot and so forth. Flavors which have been found to be particularly useful include commercially available strawberry, orange, grape, cherry, vanilla, mint and citrus flavors and mixtures thereof. The amount of flavoring may depend on a number of factors, including the organoleptic effect desired. Flavors will be present in any amount as desired by those of ordinary skill in the art.

The compositions of the present disclosure can include a sweetener component, which can include one or more sweeteners. As used herein, the term "sweetener" is intended to mean a compound used to impart sweetness to a preparation. Such compounds include, by way of example and without limitation, aspartame, polyols such as mannitol, sorbitol and xylitol, acesulfame, neotame, *stevia*, dextrose, saccharin sodium, fructose, high fructose corn syrup, maltodextrin, sucralose, sucrose, and other materials known to one of ordinary skill in the art, and combinations thereof.

The compositions of the present disclosure can include one or more colorants. As used herein, the term "colorant" refers to pigments and/or dyes or a combination thereof, that are used to impart color to the composition. In some embodiments, colorants include, but are not limited to, FD&C approved colorants. Examples include caramel colorant, red colorant Enocianin, Indigo yellow, Quinoline yellow, Quinizarine Green, FD&C Blue #1 Aluminum Lake, FD&C Blue #2, other FD&C Blue colors, titanium dioxide, iron oxide, and/or combinations thereof.

The pharmaceutical compositions provided herein contain therapeutically effective amounts of one or more of compounds provided herein that are useful in the treating, reducing, resolving, eliminating, ameliorating and/or preventing the conditions described herein, or one or more of the symptoms thereof. The pharmaceutical compositions comprise a solvent component comprising one or more organic solvents in an amount of from about 80% to about 120% w/v. In some embodiments, the organic solvents of the solvent component can be selected from polyethers, lower polyhydroxy alcohols, ethanol, propylene glycol, isosorbide dimethyl ether, di(ethylene glycol) ethyl ether, mineral oil; light mineral oil; glycols, such as glycerol behenate and polyethylene glycol (PEG), hydrogenated vegetable oil, including cottonseed oil, sunflower oil, sesame oil, olive oil, corn oil, soybean oil, and mixtures thereof. In some embodiments, the organic solvents of the solvent component can be selected from glycerin, polyethylene glycols, propylene glycol, and mixtures thereof. In some embodiments, the organic solvents include polyethylene glycol and glycerin. Suitable polyethylene glycols (PEGs) include all grades of PEGs, having molecular weights of from 300 to about 8000. In some embodiments, the organic solvents are selected from glycerin and polyethylene glycols of molecular weight about 300 to about 3000; or from 300 to about 1000; or from about 300 to about 600, or from 300 to about 500, or about 400 Daltons.

Further examples of useful solvents include dialkylated mono- or poly-alkylene glycols, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol.

The pharmaceutical compositions provided herein, for example Compositions 1, 1a, 1.1-1.38, 2, 2a or 2.1-2.38 are liquids, for example a solution or a suspension. In some embodiments, the pharmaceutical compositions provided herein are solutions; i.e., they contain dissolved components and no significant particulates. In some embodiments, the pharmaceutical compositions provided herein are liquids for oral administration. As used herein, the terms "oral administration" or "administering to a patient" is intended to mean that the liquid is introduced into the patient through the mouth or the nose without further dilution, or addition of other components, such that the liquid reaches the stomach. Thus, "oral administration" or "administration to the patient" includes administering through devices that are designed to deliver components to the stomach, for example a feeding tube or nasal gastric tube.

The pharmaceutical compositions provided herein may be administered at once, or in divided doses at multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations. The dosages of the compositions described herein are titratable based on weight and body size.

Dosages employed in practicing the present invention will of course vary depending, e.g. on the particular disease or condition to be treated, the particular mode of administration, and the therapy desired.

Compositions of the present disclosure are preferably administered orally. In general, satisfactory results, e.g. for the treatment of adults and pediatric patients (i.e., humans 2-16 years old) having one or more of the disorders and diseases as hereinbefore set forth, can be obtained with oral administration at daily dosages of from about 12 mg to about 1000 mg, for example from 25 mg to 1000 mg; for example from 12 mg to 800 mg, for example from 25 mg to 800 mg; for example from 12 mg to 600 mg, for example from 25 mg to 600 mg, for example from 25 mg to 400 mg for example from 25 mg to 200 mg, for example from 12 mg to 50 mg, for example from 12 mg to 25 mg, for example from 50 to 500 mg, for example from 100 to 500 mg, for example from 200 to 500 mg, for example from 300 to 500 mg, for example from 200 to 1000 mg, for example from 200-800 mg, for example from 200-600 mg, for example about 400 mg. The dosages can be conveniently administered once, or in divided dosages, for example 2 times per day, 3 times per day, or 4 times per day.

In some embodiments, the topiramate is administered in two divided doses, given in the morning and evening. In some embodiments, the dose of topiramate is 400 mg/day in two divided doses, preferably given in the morning and evening.

In some embodiments, the concentration of topiramate or pharmaceutically acceptable addition salt thereof in the present compositions is from about 1.2% w/v (i.e., 12 mg/ml) to about 10% w/v (i.e., 100 mg/ml); or from about 2.5% w/v (i.e., 25 mg/ml) to about 10% w/v (i.e., 100 mg/ml); or from about 2.5% w/v to about 8% w/v; or from about 2.5% w/v to about 6% w/v; or from about 2.5% w/v (i.e., 20 mg/ml) to about 4% w/v; or from about 2.5% w/v to about 3% w/v. In some embodiments, the concentration of topiramate or pharmaceutically acceptable addition salt thereof in the present compositions is from about 1.2% w/v (i.e., about 12 mg/ml) to about 2.5% w/v; for example, about 2.5% w/v (i.e., about 25 mg/ml).

In some embodiments, the topiramate compositions of the present disclosure, i.e., Compositions 1, 1a, 1.1-1.38, 2, 2a or 2.1-2.38 are provided as ready-to-use liquid preparations, in a dosage dispensing unit. The dosage dispensing unit can be any container that is known in the medical arts to be useful for storing liquid pharmaceuticals prior to administration, and from which portions of the contents, for example specific doses to be administered to a patient, can be withdrawn. In some embodiments, the dosage dispensing unit is a bottle comprising a septum, from which quantities of the Composition can be withdrawn.

In some embodiments, a desired quantity of the topiramate composition is removed from the dosage dispensing unit and placed in a direct dosing device, which is a device or container that is used to administer its contents directly to a patient. Examples of such direct dosing devices include, but are not limited to, syringes, for example oral syringes, cups, and other vehicles that are used for administering oral liquids to the mount of a patient. In some embodiments, the direct dosing device is an oral syringe. Thus, in some such embodiments, the oral syringe is inserted through the septum of the dosage dispensing device, and a desired amount of topiramate composition is drawn into the syringe. The syringe is then used to administer the topiramate composition directly into the patient's mouth.

In some embodiments, administration of a desired dosage of topiramate is achieved by varying the amount of the topiramate composition withdrawn from the dosage dispensing device by the direct dosing device. For example, for a dosage dispensing device (e.g., a bottle with a septum as described herein) containing a 2.5% w/v (25 mg/ml) topiramate composition in accordance with the present disclosure, withdrawal of from 1 ml to 16 ml of topiramate by a direct dosing device (e.g. an oral syringe) affords delivery of from 25 mg to 400 mg of topiramate, or pharmaceutically acceptable salt thereof, to the patient. Thus, for the titration shown below in Table 3, the morning and evening doses during the six week titration period, using a 2.5% w/v (25 mg/ml) topiramate composition in accordance with the present disclosure, would be each be 1 ml in week 1; 2 ml in week 2; 3 ml in week 3; 4 ml in week 4; 6 ml in week 5; and 8 ml in week 6 and beyond.

In some embodiments, the topiramate compositions of the present disclosure, i.e., Compositions 1, 1a, 1.1-1.38, 2, 2a or 2.1-2.38 are bioequivalent to commercially available TOPAMAX® capsule. As used herein, "commercially available TOPAMAX® capsule" is intended to mean TOPAMAX® capsules sold by Janssen Pharmaceuticals as disclosed in "HIGHLIGHTS OF PRESCRIBING INFORMATION" (revised June 2020) available from the Janssen TOPAMAX® web site at: http://www.janssenlabels.com/package-insert/product-monograph/prescribing-information/TOPAMAX-pi.pdf, the content of which is incorporated herein by reference. In one aspect, the TOPAMAX® capsules are 25 mg Sprinkle Capsules that contain topiramate-coated beads in a hard gelatin capsule. The inactive ingredients are black pharmaceutical ink, cellulose acetate, gelatin, povidone, sodium lauryl sulfate, sorbitan monolaurate, sugar spheres comprising sucrose and starch, and titanium dioxide.

As used herein, the term "bioequivalent" is intended to mean that the composition exhibits a total amount of topiramate absorbed that is bioequivalent to a commercially available capsule (TOPAMAX®) composition containing 25 mg of topiramate upon administration to a human subject, wherein the bioequivalence of the total amount of topiramate absorbed is established by a 90% confidence interval for $AUC_{0-\infty}$ and $AUC_{0-t}$ which is between 80% and 125% upon administration with or without food.

EXAMPLES

The following examples are further illustrative of the nature of the present invention, but it is understood that the invention is not limited thereto. All amounts and proportions referred to herein and in the appended claims are by weight, unless otherwise indicated.

Example 1—Preparation of Topiramate Formulation

Topiramate formulations in accordance with the present disclosure is prepared containing the following ingredients:

TABLE 1

Topiramate Formulation Composition

| Ingredients | % w/v | g |
| --- | --- | --- |
| Polyethylene Glycol 400 | 50 | 1500 |
| Methylparaben | 2.16 | 64.8 |
| Propylparaben | 0.24 | 7.2 |
| Glycerin | 40 | 1200 |
| Topiramate | 2.5 | 75 |
| Sucralose | 1 | 30 |
| Flavor | 0.2 | 6 |
| Glycerin | to 100 mL* | to 3000 mL |

*density: 1.2 g/ml

Methylparaben and propylparaben are added to polyethylene Glycol 400 and mixed. The sucralose and topiramate are then each added individually with mixing until dissolved. The flavor is then added with mixing, followed by glycerin, also with mixing. The final solution is optionally filtered, and then packaged into a 16 oz white HDPE bottle with 28 mm CRC closures with induction foil.

Example 2—Stability of Formulation

Samples of the Topiramate formulation from Example 1 were stored for six months 4° C., at 25° C./60% relative humidity and 40° C./75% relative humidity. All samples were assayed at 3 months, and the 4° C. and 25° C./60% RH samples were assayed at 6 months. The Table below shows the results for methylparaben, propylparaben, and impurities Compound A (a related breakdown product), sulfate, sulfamate and fructose.

TABLE 2

Stability of Topiramate Formulation

| Stability Conditions | Assay, % | % Methyl-paraben | % Propyl-paraben | % Compound A | % Sulfate | % Sulfamate | % Fructose |
|---|---|---|---|---|---|---|---|
| Initial | 100.2 | 98.8 | 99.28 | 0.03 | ND | <LOD | <LOD |
| 3 month-4° C. | 99.8 | 98.5 | 98.5 | 0.03 | ND | ND | <LOD |
| 6 month-4° C. | 100.3 | 100.1 | 101.1 | 0.04 | ND | ND | <LOD |
| 3 month-25° C./60% RH | 99.1 | 99.1 | 98.8 | 0.06 | ND | ND | <LOD |
| 6 month-25° C./60% RH | 100.3 | 100.4 | 101.5 | 0.04 | ND | ND | ND |
| 3 month-40° C./75% RH | 97.7 | 98.6 | 98.3 | 0.14 | <LOD | ND | <LOD |

As can be seen, the Topiramate formulation is extremely stable at room temperature (25° C./60% RH). Based on extrapolation of 3 month accelerated shelf stability data, the Topiramate formulation is extremely stable at room temperature/60% RH for at least two years.

Example 3—Titration of Topiramate Solution

In some embodiments, the compositions of the present disclosure are useful as initial monotherapy in patients 2 years of age and older with partial onset or primary generalized tonic-clonic seizures. In some embodiments, the compositions of the present disclosure are useful as adjunctive therapy for adults and pediatric patients 2 to 16 years of age with partial onset seizures or primary generalized tonic-clonic seizures, and in patients 2 years of age and older with seizures associated with Lennox-Gastaut syndrome. In further embodiments, the compositions of the present disclosure are useful for the prophylaxis of migraine headache.

In some embodiments, the dose is achieved by titration. For example, a 200 mg dose given twice daily is preferably achieved according to the following schedule in Table 3:

TABLE 3

Monotherapy Titration Schedule for Adults and Pediatric Patients 10 years and older

| | Morning Dose | Evening Dose |
|---|---|---|
| Week 1 | 25 mg | 25 mg |
| Week 2 | 50 mg | 50 mg |
| Week 3 | 75 mg | 75 mg |
| Week 4 | 100 mg | 100 mg |
| Week 5 | 150 mg | 150 mg |
| Week 6 | 200 mg | 200 mg |

The formulation from Example 1 is administered to a patient in need thereof via an oral syringe twice daily in accordance with the schedule shown in Table 3 above. 1 ml (25 mg topiramate) of the composition of Example 1 is drawn into an oral syringe and administered directly to the mouth of an adult patient in need thereof twice daily for the first week of treatment. The procedure is repeated with 2 ml twice daily in week 2; 3 ml twice daily in week 3; 4 ml twice daily in week 4; 6 ml twice daily in week 5; and 8 ml twice daily in week 6 and beyond.

8 ml (200 mg topiramate) of the composition of Example 1 is drawn into an oral syringe and administered directly to the mouth of an adult patient in need thereof twice daily for the course of treatment.

Example 4—Administration of Topiramate Solution—Maintenance

The formulation from Example 1 is administered to a patient in need thereof via an oral syringe. 8 ml (200 mg topiramate) of the composition of Example 1 is drawn into an oral syringe and administered directly to the mouth of an adult patient in need thereof twice daily for the course of treatment.

Example 5—Dosing in Pediatric Patients

Dosing in patients 2 to 9 years of age is based on weight. During the titration period, the initial dose of topiramate is 25 mg/day nightly for the first week. Based upon tolerability, the dosage can be increased to 50 mg/day (25 mg twice daily) in the second week. Dosage can be increased by 25-50 mg/day each subsequent week as tolerated. Titration to the minimum maintenance dose is preferably attempted over 5-7 weeks of the total titration period. Based upon tolerability and clinical response, additional titration to a higher dose (up to the maximum maintenance dose) can be attempted at 25-50 mg/day weekly increments. The total daily dose preferably does not exceed the maximum maintenance dose for each range of body weight, as shown below in Table 4:

TABLE 4

Monotherapy Target Total Daily Maintenance Dosing for Patients 2 to 9 Years of Age

| Weight (kg) | Total Daily Dose (mg/day). Minimum Maintenance Dose | Total Daily Dose (mg/day). Maximum Maintenance Dose |
|---|---|---|
| Up to 11 | 150 mg | 250 mg |
| 12-22 | 200 mg | 300 mg |
| 23-31 | 200 mg | 350 mg |
| 32-38 | 250 mg | 350 mg |
| Greater than 38 | 250 mg | 400 mg |

Example 6—Dosing in Adjunctive Therapy
Epilepsy

Adults (17 Years of Age and Over)

Compositions of the present disclosure can be used to provide a total daily dose of topiramate or a pharmaceutically acceptable addition salt thereof as adjunctive therapy in adults with partial onset seizures or Lennox-Gastaut Syndrome. Preferably, the dosage is 200 to 400 mg/day in two divided doses, and 400 mg/day in two divided doses as adjunctive treatment in adults with primary generalized tonic-clonic seizures. A composition in accordance with the present disclosure is administered to provide 25 to 50 mg/day, followed by titration to an effective dose in increments of 25 to 50 mg/day every week. Titrating in increments of 25 mg/day every week may delay the time to reach an effective dose. Doses above 400 mg/day have not been shown to improve responses in adults with partial onset seizures.

Pediatric Patients 2 to 16 Years of Age

A composition in accordance with the present disclosure is administered to pediatric patients with partial onset seizures, primary generalized tonic-clonic seizures, or seizures associated with Lennox-Gastaut syndrome that is sufficient to provide 5 to 9 mg/kg/day in two divided doses.

Titration should begin at 25 mg/day (or less, based on a range of 1 to 3 mg/kg/day) nightly for the first week. The dosage should then be increased at 1- or 2-week intervals by increments of 1 to 3 mg/kg/day (administered in two divided doses), to achieve optimal clinical response. Dose titration should be guided by clinical outcome. The total daily dose should not exceed 400 mg/day.

Example 7—Dosing in Migraine Prophylaxis

A composition in accordance with the present disclosure is administered to patients 12 years of age and older for prophylaxis of migraine headache. The dose is titrated up to 100 mg/day administered in two divided doses, as shown below in Table 5.

TABLE 5

Migraine Prophylaxis Titration Schedule for
Patients 12 Years of Age and Older

| Weight (kg) | Morning Dose | Evening Dose |
|---|---|---|
| Week 1 | None | 25 mg |
| Week 2 | 25 mg | 25 mg |
| Week 3 | 25 mg | 50 mg |
| Week 4 | 50 mg | 50 mg |

Additional information relevant to Topiramate generally can be found in the product label for Topamax®, which is incorporated by reference herein in its entirety.

Example 8—Topiramate Oral Solution Relative Bioavailability Study

An Open-Label, Randomized, Single-Dose, Three-Period, Three-Sequence, Three-Way Crossover, Fasting Relative Bioavailability Study of Topiramate Oral Solution 25 mg/mL was conducted versus TOPAMAX® (Topiramate capsule) Sprinkle Capsule 25 mg and Food-Effect Study on Topiramate Oral Solution 25 mg/mL in Normal, Healthy, Adult, Non-Smoking Male Subjects The pharmacokinetic parameters were calculated from the plasma concentration vs. time profile by non-compartmental model using Phoenix® WinNonlin® Version 8.1 (Certara L.P.) for Topiramate. Statistical comparison of the pharmacokinetic parameters of the three formulations was carried out using PROC MIXED of SAS® Version 9.4 (SAS Institute Inc., USA) to assess the bioavailability between Test Product-T1 (under fasting condition) vs. Reference Product-R (under fasting condition) and evaluation of the food effect between Test Product-T2 (Under fed condition) vs. Test Product-T1 (Under fasting condition).

| | |
|---|---|
| Test Product-T1 & T2 | Topiramate oral solution 25 mg/ml |
| Reference Product-R | TOPAMAX ® (Topiramate capsule) sprinkle capsule 25 mg |

Dose and Mode of Administration:

For Test Product T1 and Reference Product-R

After an overnight fast of at least 10 hours, a single oral dose (1 mL solution of Test Product-T1 or 25 mg sprinkle capsule of Reference Product-R) was administered with 240±2 mL of drinking water at ambient temperature to the subjects in sitting posture at 0.00 hour on Day 1 of each study period. The IMP administration was as per the randomization schedule and under open label conditions.

For Test Product T2

After an overnight fast of at least 10 hours, the subjects were served a high fat meal, which they consumed completely within 30 minutes.

A single oral dose (1 mL solution of Test Product-T2) was administered at 30 minutes after serving of a high fat meal to the subjects in sitting posture with 240±2 mL of drinking water at ambient temperature at 0.00 hour on Day 1 of each study period. The Investigational Medicinal Product (IMP) administration was as per the randomization schedule and under open label conditions.

The study drugs were swallowed whole (for test and reference products) and reference product was not crushed or chewed.

Test Product-T1 (Under fasting condition) vs. Reference Product-R (Under fasting condition): The relative bioavailability analyses (i.e. geometric least squares means, ratio, 90% confidence interval, intra subject CV and power) of Test Product-T1 (under fasting condition) vs. Reference Product-R (under fasting condition) for Topiramate are summarized in the following table:

Relative Bioavailability Results for Topiramate (N = 22)
[Excluding particular period of subjects whose pre-dose concentration was >5% of Cmax]

| | Geometric Least Squares Means | | | | | |
|---|---|---|---|---|---|---|
| Parameters | Test Product-T1 (N = 21) | Reference Product-R (N = 22) | Ratio (T1/R) % | 90% Confidence Interval | Intra Subject CV (%) | Power (%) |
| $lnC_{max}$ | 281.635 | 249.501 | 112.9 | 105.93-120.28 | 11.9 | 100.0 |
| $lnAUC_{0-t}$ | 11582.446 | 11881.573 | 97.5 | 95.06-99.96 | 4.7 | 100.0 |
| $lnAUC_{0-\infty}$ | 19689.317 | 19410.206 | 101.4 | 95.79-107.42 | 10.7 | 100.0 |

The relative bioavailability analyses (i.e. geometric least squares means, ratio, 90% confidence interval, intra subject CV and power) of Test Product-T2 (under fed condition) vs. Test Product-T1 (under fasting condition) for Topiramate are summarized in the following table:

Relative Bioavailability Results for Topiramate (N = 22)
[Excluding particular period of subjects whose pre-dose concentration was >5% of Cmax]

| | Geometric Least Squares Means | | | | | |
|---|---|---|---|---|---|---|
| Parameters | Test Product-T2 (N = 16) | Test Product-T1 (N = 21) | Ratio (T2/T1) % | 90% Confidence Interval | Intra Subject CV (%) | Power (%) |
| $lnC_{max}$ | 202.669 | 282.879 | 71.6 | 66.92-76.70 | 11.1 | 99.9 |
| $lnAUC_{0-t}$ | 11160.586 | 11579.467 | 96.4 | 93.88-98.95 | 4.1 | 100.0 |
| $lnAUC_{0-\infty}$ | 19113.162^ | 19602.192 | 97.5 | 91.43-103.99 | 9.9 | 100.0 |

The Mean Plasma Concentration vs. Time curve for Topiramate is shown in FIG. 1.

Test Product-T1 (under fasting condition) when compared with Reference Product-R (under fasting condition) the test to reference ratio of $AUC_{0-t}$ and $AUC_{0-\infty}$ for Test Product-T1 and Reference Product-R are close to 100%. However, the test to reference ratio of C max is ~13% higher as compared to reference product.

However, 90% Confidence Interval of ln-transformed data of $C_{max}$, $AUC_{0-\infty}$ and $AUC_{0-\infty}$ were within the USFDA (Bioequivalence Studies with Pharmacokinetic Endpoints for Drugs Submitted Under an ANDA; December 2013) regulatory defined acceptance criteria of 80.00-125.00% to consider two formulations as bioequivalent. In line with the same, the rate and extent of absorption of Topiramate from Test Product-T1 are comparable with Reference Product-R under fasting condition and obtained difference of ~13% in C max has no clinical relevance. Hence, both Test Product-T1 (Topiramate Oral Solution 25 mg/mL) and Reference Product-R (TOPAMAX® Sprinkle Capsule 25 mg) are considered bioequivalent under fasting condition.

Test Product-T2 (under fed condition) when compared with Test Product-T1 (under fasting condition) for the food effect, the Test Product-T2 to Test Product-T1 ratio of C max is found 71.6% which is low. However, the Test Product-T2 to Test Product-T1 ratio of $AUC_{0-t}$ and $AUC_{0-\infty}$ is found 96.4% and 97.5%, respectively The median T max in hours (range) for T1 (fasting) was 0.500 (0.333-1.250), and for T2 (fed) was 5.509 (3.000-8.000).

In presence of food, peak concentration of Topiramate is reduced by ~28.4% with median T max delayed by ~5 hours as compared to fasting condition after oral administration of Topiramate Oral Solution 25 mg/mL. Since, 90% Confidence interval of ln-transformed data $AUC_{0-t}$ and $AUC_{0-\infty}$ were within the USFDA regulatory (Bioequivalence Studies with Pharmacokinetic Endpoints for Drugs Submitted Under an ANDA; December 2013) defined criteria of 80.00-125.00 for equivalence, we can conclude that the extent of absorption of the Topiramate is not affected in presence of food after oral administration of Topiramate Oral Solution 25 mg/mL.

While the invention has been described in connection with what is presently considered to be the most practical and preferred embodiment, it is to be understood that the invention is not to be limited to the disclosed embodiments, but to the contrary, it is intended to cover various modifications or equivalent arrangements included within the spirit and scope of the appended claims. The scope is to be accorded the broadest interpretation so as to encompass all such modifications and equivalent structures as is permitted under the law.

Each of the patents, books, articles and other printed publications referenced herein are incorporated by reference in their entireties for all purposes.

What is claimed is:

1. A method for treating a disease or disorder, or a symptom thereof, consisting of orally administering to a patient in need thereof a pharmaceutical composition,
    wherein the pharmaceutical composition is an oral liquid pharmaceutical composition, wherein the liquid pharmaceutical composition is formulated as a solution and wherein the pharmaceutical composition consists of:
    (1) topiramate, or a pharmaceutically acceptable addition salt thereof, in an amount of about 25 mg/ml in the liquid pharmaceutical composition;
    (ii) a solvent component comprising one or more organic solvents in an amount of from about 80% to about 120% w/v in the liquid pharmaceutical composition, wherein the solvent component consists of glycerin in an amount of 60% to 65% w/v and polyethylene glycol of molecular weight about 400 in an amount of 45% to 55% w/v;

(iii) one or more preservatives selected from parabens, benzyl alcohol, benzoic acid, sorbic acid, sodium benzoate, and ascorbic acid;
(iv) one or more sweeteners; and
(v) a flavor component;
wherein the liquid pharmaceutical composition is administered to the patient at 25 mg/ml of topiramate, or a pharmaceutically acceptable addition salt thereof,
wherein the pharmaceutical composition is substantially anhydrous, wherein the disease or disorder, or symptom thereof, is selected from: epilepsy, onset seizures, primary generalized tonic-clonic seizures, seizures associated with Lennox-Gastaut syndrome, and migraine.

2. The method of claim 1 wherein the composition is administered to the patient from a direct dosing device.

3. The method of claim 2, wherein the direct dosing device is a measuring device with graduations.

4. The method of claim 2, wherein the direct dosing device is an oral syringe.

5. The method of claim 1, wherein the patient is not a pediatric patient.

6. The method of claim 1, wherein the patient is from 2-16 years old.

7. The method of claim 1, wherein the patient is an adult.

8. The method of claim 2, further comprising the step of filling the direct dosing device with the composition by withdrawing said composition from a dosage dispensing unit.

9. The method of claim 8, wherein the amount of the liquid pharmaceutical composition transferred to the direct dosing device is sufficient to provide from 12 mg to 1000 mg of topiramate or a pharmaceutically acceptable addition salt thereof.

10. The method of claim 1, wherein the liquid pharmaceutical composition consists of the following components:
(i) polyethylene glycol 400 in an amount of about 50% w/v;
(ii) one or more parabens in an amount of about 2.4% w/v;
(iii) glycerin in an amount of 60% w/v to 65% w/v;
(iv) topiramate, or a pharmaceutically acceptable addition salt thereof, in an amount of about 25 mg/ml;
(v) one or more sweeteners in an amount of about 1% w/v; and
(vi) a flavor component comprising one or more flavor compounds, the flavor component being in an amount of about 0.2% w/v.

11. The method of claim 1, wherein the liquid pharmaceutical composition has one or more of the following features:
(a) a refractive index of from about 1.3 to about 1.38;
(b) a viscosity of 300-600 cps; or
(c) a density of 1.1-1.3.

12. The method of claim 1, wherein the topiramate is in the form of a free acid.

13. The method of claim 1, wherein the solvent component consists of:
polyethylene glycol 400 in an amount of about 50% w/v; and
glycerin in an amount of about 63% w/v.

14. The method of claim 1, wherein the disease or disorder, or symptom thereof, is partial-onset seizures.

15. The method of claim 1, wherein the disease or disorder, or symptom thereof, is a primary generalized tonic-clonic seizure.

16. The method of claim 1, wherein the disease or disorder, or symptom thereof, is a seizure associated with Lennox-Gastaut syndrome.

17. The method of claim 1, wherein the disease or disorder, or symptom thereof, is migraine.

* * * * *